United States Patent [19]  [11] 4,119,647
Liebman et al.  [45] Oct. 10, 1978

[54] 25-HYDROXYCHOLECALCIFEROL-23,24-³H AND PROCESS FOR THE PREPARATION THEREOF

[75] Inventors: Arnold Alvin Liebman, Upper Saddle River; Richard Robert Muccino, Verona, both of N.J.

[73] Assignee: Hoffmann-La Roche Inc., Nutley, N.J.

[21] Appl. No.: 786,158

[22] Filed: Apr. 11, 1977

[51] Int. Cl.² .............................................. C07J 9/00
[52] U.S. Cl. .......................... 260/397.2; 260/239.55 R
[58] Field of Search ...................................... 260/397.2

[56] References Cited
U.S. PATENT DOCUMENTS 3,833,622  9/1974  Babcock et al. .................. 260/397.2

Primary Examiner—Elbert L. Roberts
Attorney, Agent, or Firm—Samuel L. Welt; George M. Gould; Raymond R. Wittekind

[57] ABSTRACT

25-Hydroxycholecalciferol-23,24-³H and process for the preparation thereof are disclosed. 25-Hydroxycholecalciferol-23,24-³H is useful in radioimmunoassay for the detection of 25-hydroxycholecalciferol, a physiologically important metabolite of cholecalciferol (vitamin $D_3$).

7 Claims, No Drawings

25-HYDROXYCHOLECALCIFEROL-23,24-³H AND PROCESS FOR THE PREPARATION THEREOF

BACKGROUND OF THE INVENTION

Cholecalciferol (vitamin D₃) is hydroxylated in the liver to 25-hydroxycholecalciferol. This metabolite, which, like the parent vitamin, promotes bone calcium mobilization and stimulates intestinal calcium transport, and serves as a precursor for the physiologically active form, 1,25-dihydroxycholecalciferol, of the vitamin is present in relatively low levels in the circulatory system. See J. L. Omdahl and H. F. DeLuca, Physiological Reviews, 53, 327 (1973) and H. K. Schnoes and H. F. DeLuca, Vitamins and Hormones, 32, 385 (1974). To detect these relatively low blood levels of 25-hydroxycholecalciferol by radioimmunological techniques requires the tritium labelling of the metabolite in very high specific activity. See, for example, W. T. Newton and B. M. Jaffe in "Radioassay In Clinical Medicine", W. T. Newton and R. M. Donati, ed., Charles C. Thomas, Springfield, Ill., 1974, pages 13 to 17.

The desired labelling of 25-hydroxycholecalciferol has been accomplished by two reported procedures (T. Suda et al., Analyt. Biochem., 43, 139 [1971] and P. A. Bell and W. P. Scott, J. Labelled Compounds, 9, 339 [1973]). The first involves the addition of tritio-methyl Grignard to 25-keto-7-dehydrocholesterol (I) followed by photolysis and thermolysis of the intermediate provitamin II to yield 25-hydroxycholecalciferol-26(27)-³H (III). The second involves the addition of the same Grignard reagent to 25-ketocholecalciferol (IV) to afford directly the labelled metabolite III. As noted, both prior processes utilize tritio-methyl Grignard reagent, prepared from formaldehyde and sodium borotritide having one atom of tritium per mole of Grignard reagent to introduce the label. As such, the introduction of the label is limited to one tritium atom per molecule of 25-hydroxycholecalciferol, resulting in the labelled metabolite having a specific activity of up to about 10 Ci/mmole. Thus, it is apparent that to achieve the labelled metabolite with the requisite high specific activity would require multiple labelling with fully enriched tritium, i.e., the addition of molecular tritium to an unsaturated system prior to elaboration of the extended olefinic system of the metabolite.

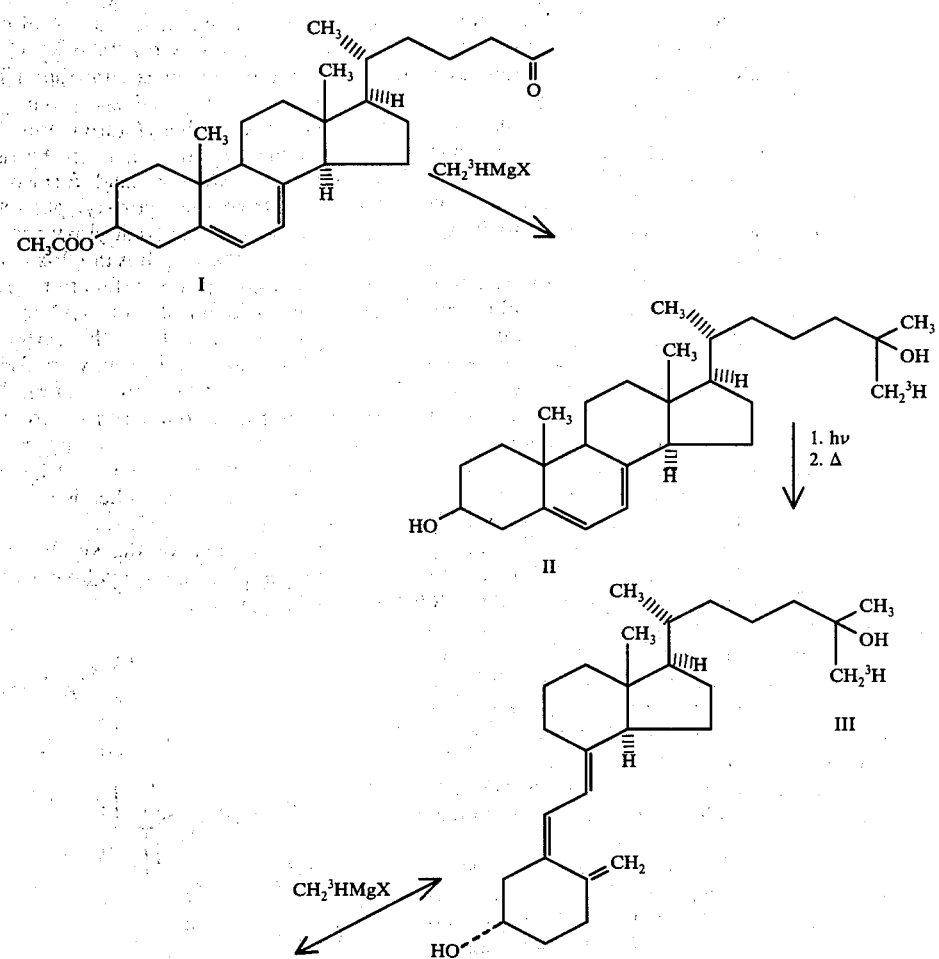

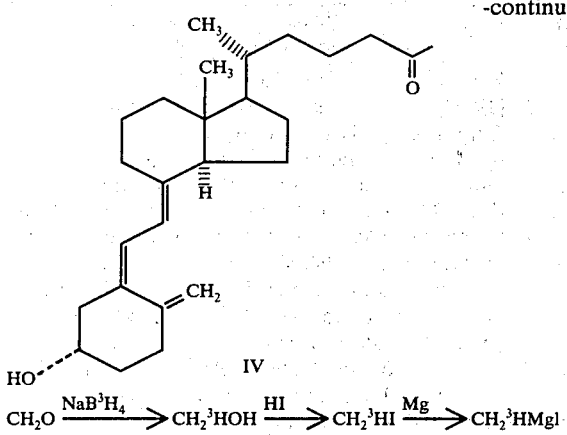

IV

CH$_2$O $\xrightarrow{\text{NaB}^3\text{H}_4}$ CH$_2$$^3$HOH $\xrightarrow{\text{HI}}$ CH$_2$$^3$HI $\xrightarrow{\text{Mg}}$ CH$_2$$^3$HMgI The present invention relates to 25-hydroxycholecalciferol-23,24-$^3$H having the requisite high specific activity and to a novel efficient process for the preparation thereof from readily available precursors involving the addition of two molecules of tritium to an acetylenic linkage. More particularly, the present process aspect relates to a method of synthesizing 25-hydroxycholecalciferol-23,24-$^3$H comprising the steps of rearranging 3β,25-dihydroxy-3α,5-cyclo-5α-cholest-23-yne, in which the hydroxy groups may be conventionally protected by ether moieties, to 3β,25-dihydroxycholest-5-en-23-yne 3-acylate, acylating 3β,25-dihydroxy-cholest-5-en-23-yne 3-acylate to 3β,25dihydroxy-cholest-5-en-23-yne. 3β,25-diacylate, tritiating 3β,25-dihydroxycholest-5-en-23-yne 3β,25-diacylate to 25-hydroxycholesterol-23,24-$^3$H diacylate, converting 25-hydroxycholesterol-23,24-$^3$H diacylate to 25-hydroxy-7-dehydrocholesterol-23,24-$^3$H diacylate, hydrolyzing 25-hydroxy-7-dehydrocholesterol-23,24-$^3$H diacylate to 25-hydroxy-7-dehydrocholesterol-23,24-$^3$H, irradiating 25-hydroxy-7-dehydrocholesterol-23,24-$^3$H to 25-hydroxyprecholecalciferol-23,24-$^3$H and isomerizing 25-hydroxyprecholecalciferol-23,24-$^3$H to 25-hydroxycholecalciferol-23,24-$^3$H.

In the formulas presented herein, the various substituents are illustrated as joined to the steroid and cholecalciferol nuclei by one of three notations: a solid line (—) indicating a substituent which is in the 62-orientation (i.e., above the plane of the molecule), a dotted line (- - -) indicating a substituent which is in the α-orientation (i.e., below the plane of the molecule), or a wiggly line (⌇) indicating a substituent which may be in the α- or β-orientation or may be a mixture of both forms. The formulas have all been drawn to show the compounds in their absolute sterochemical configurations. Since the starting materials are derived from naturally occurring materials, the final products exist in the single absolute configuration depicted herein. However, the processes of the present invention are intended to apply as well to the synthesis of steroids of the racemic series. Thus, one may begin the synthesis utilizing racemic starting materials to prepare racemic products. Optically active products can then be prepared by resolution of the racemic products utilized in the preparation thereof, as hereinafter described, by standard resolution techniques well-known in the art.

As used throughout the specification and the appended claims, the term "alkyl group" refers to a monovalent substituent consisting solely of carbon and hydrogen of from 1 to 20 carbon atoms which may be straight or branched-chain. Examples of alkyl groups are methyl, ethyl, n-propyl, i-propyl, tert-butyl, hexyl, octyl and so forth. The term "alkylene group" refers to a divalent substituent consisting solely of carbon and hydrogen of from 1 to 20 carbon atoms which may be straight or branched-chain and whose free valences are attached to two distinct groups. Examples of alkylene groups are methylene, ethylene, propylene, butylene and so forth. The term "alkoxy group" refers to a monovalent substituent which consists of an alkyl group linked through an ether oxygen having its free valence bond from the ether oxygen. Examples of alkoxy groups are methoxy, ethoxy, isopropoxy, tert-butoxy and so forth. The term "phenyl alkoxy" refers to an alkoxy group which is substituted by a phenyl ring. Examples of phenyl alkoxy groups are benzyloxy, 2-phenylethoxy, 4-phenylbutoxy and so forth. The term "alkanoyloxy group" refers to the residue of an alkylcarboxylic, an alkanoic acid, formed by removal of the hydrogen from the hydroxyl portion of the carboxyl group. Examples of alkanoyloxy groups are formyloxy, acetoxy, butyryloxy, hexanoyloxy and so forth. The term "alkanoyl group" refers to the residue of an alkylcarboxylic acid, an alkanoic acid, formed by removal of the hydroxy group from the carboxylic acid moiety. Examples of alkanoyl groups are formyl, acetyl, butyryl, hexanoyl and so forth. The term "lower" as applied to any of the aforementioned groups refers to those groups having from 1 to 8 carbon atoms. The Greek letter xi (ξ) in the name of a cholecalciferol intermediate indicates that the stereochemistry of the substituent to which it refers is undefined.

In the first step of the synthetic sequence for the preparation of 25-hydroxycholecalciferol-23,24-$^3$H, an i-steroid of formula V

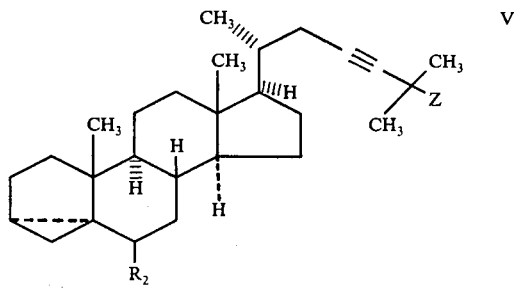

wherein $R_2$ is hydroxy, lower alkoxy, phenyl lower alkoxy, lower alkanoyloxy or benzoyloxy and Z is hydroxy or a group of the formula

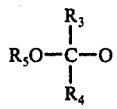

ps wherein $R_3$ is hydrogen or lower alkyl, $R_4$ and $R_5$ are each independently lower alkyl and $R_4$ and $R_5$ taken together are lower alkylene of from 3 to 8 carbon atoms the preparation of which is described in U.S. Pat. No. 3,822,254 granted July 2, 1974, is rearranged to a cholesteryl compound of formula VI

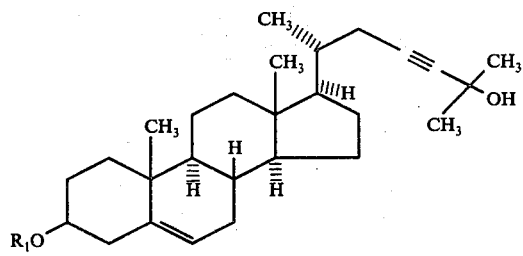

VI wherein $R_1$ is lower alkanoyl.

The rearrangement is conveniently performed by treating the compound of formula V with an alkanoic acid of formula VII $R_1OH$              VII wherein $R_1$ is lower alkanoyl at an elevated temperature within the range of about 40° C. to about 100° C. A reaction temperature of from about 50° C. to about 90° C. is preferred, a reaction temperature of about 80° C. being particularly preferred. Among suitable alkanoic acids there may be mentioned formic acid, acetic acid, butyric acid, hexanoic acid and the like, acetic acid being most preferred.

In the next step of the reaction sequence, the 25-hydroxy group of the compound of formula VI is acylated to a compound of formula VIII

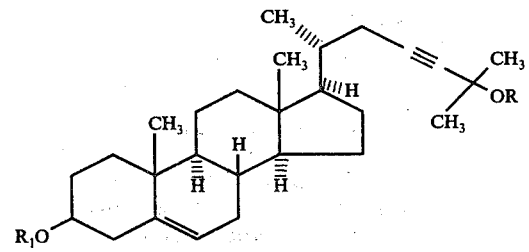

VIII wherein R and $R_1$ are each independently lower alkanoyl.

The acylation is conveniently accomplished by treating a compound of formula VI with a symmetrical alkanoic acid anhydride of formula IX $(R)_2O$             IX wherein R is as above in the presence of an acid acceptor. Suitable symmetrical alkanoic acid anhydrides include formic anhydride, acetic anhydride, propionic anhydride, hexanoic anhydride, octanoic anhydride and the like. Of these, acetic anhydride is most preferred as the acylating agent. Suitable acid acceptors include organic tertiary amine bases, both aliphatic and heterocyclic, such as, for example, triethylamine, tripropylamine, pyridine, picoline, lutidine, collidine, quinoline, 1,5-diazobicyclo(5.4.0)undec-5-ene and the like. Triethylamine and pyridine are the preferred organic tertiary amine bases for the acylation of the ethynyl carbinol VI. Pyridine is most preferred. The acylation is suitably performed using an excess of from about 1.1 to 150 moles of acylating agent per mole of carbinol at a reaction temperature from about 25° C. to the boiling point of the reaction medium. To promote the acylation about 100 moles of alkanoic acid anhydride per mole of carbinol and a reaction temperature of about 100° C. are preferably employed. It is also advantageous to use the organic tertiary amine as the solvent medium.

In the next reaction step, the step in which the label is introduced, the acetylenic compound of formula VIII is tritiated utilizing two moles of molecular tritium, to afford the saturated compound of formula X

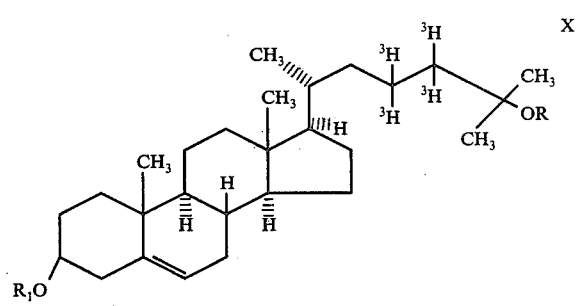

X wherein R and $R_1$ are as above having a specific activity greater than about 30 Ci/mmole.

The tritiation is conducted according to methods known per se for saturating such triple bonds and is carried out in the presence of a metal hydrogenation catalyst commonly employed in the art; suitable metal catalysts are nickel and noble metal catalysts such as platinum, palladium, rhodium and so forth. The catalysts employed are normally utilized in a finely divided state and may be either unsupported or present in a suitable inert catalyst support. As catalyst supports which may be utilized for the present reaction, there may be mentioned, among others, charcoal, diatomaceous earth, calcium carbonate, alumina and so forth.

The quantity of catalyst which may be employed is not narrowly critical and the amount of catalyst (including support) can vary from about 1 to about 100 weight percent, relative to the compound being hydrogenated. It is generally preferred to utilize between about 50 to about 90 weight percent of catalyst, the metal catalyst being present in the support in a range from about 2 to about 20 weight percent. A particularly preferred catalyst system for the tritiation comprises palladium on a carbon support.

As solvents for the hydrogenation reaction, there may be mentioned, among others, ethers such as diethyl ether, tetrahydrofuran and dioxane; alcohols such as methanol or ethanol; esters such as ethyl acetate; and so forth.

The conditions of temperature and pressure for the tritiation reaction are not narrowly critical. The reaction is conveniently performed at about, or slightly above, atmospheric pressure, although somewhat higher pressures can be employed. The reaction temperature may vary from about 0° C. to elevated temperature of about 100° C., depending upon the solvent medium and the pressure employed. For convenience, it is preferred to carry out the present hydrogenation at about room temperature.

The tritiated compound of formula X is then converted to 25-hydroxycholecalciferol-23,24-$^3$H (XV) by a series of transformations well-known in the art (see, for example, U.S. Pat. No. 3,993,675 granted Nov. 23, 1976 and references cited therein), involving the steps of allylically halogenating a tritiated compound of formula X to a 25-acyloxy-7 ξ-halocholesterol-3-acylate of formula XI

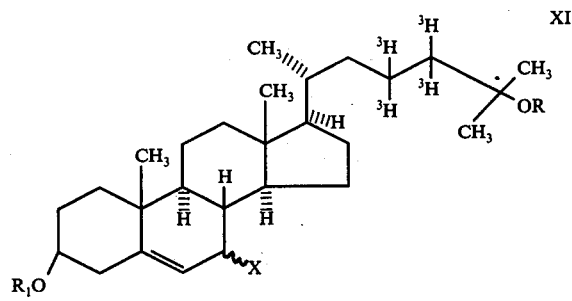

wherein R and $R_1$ are as above and X is chloro or bromo, dehydrohalogenating the 7ξ-halocholesterol of formula XI to a tritiated 7-dehydrocholesterol of formula XII

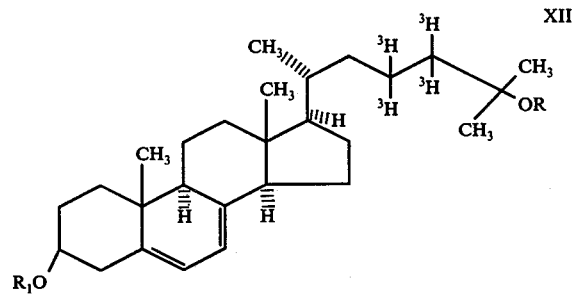

wherein $R_1$ and R are as above, having a specific activity greater than about 30 Ci/mmole, preferably about 92 Ci/mmole, saponifying the 25-acyloxy-7-dehydrocholesterol-3-acylate of formula XII to 25-hydroxy-7-dehydrocholesterol-23,24-$^3$H of formula XIII

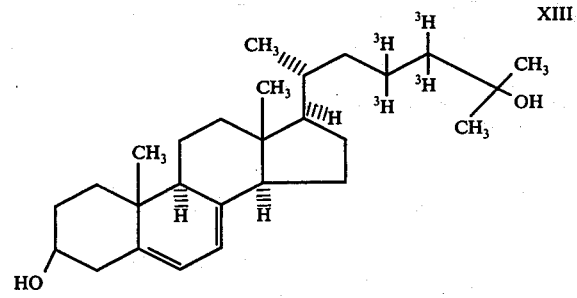

having a specific activity greater than about 30 Ci/mmole, preferably about 92 Ci/mmole, irradiating the 5,7-diene of formula XIII to the previtamin, 25-hydroxyprecholecalciferol-23,24-$^3$H, of formula XIV

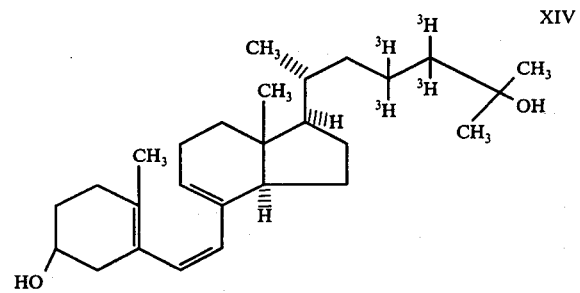

having a specific activity greater than about 30 Ci/mmole, preferably about 92 Ci/mmole, and finally isomerizing the previtamin of formula IX to 25-hydroxycholecalciferol-23,24-$^3$H of formula XV

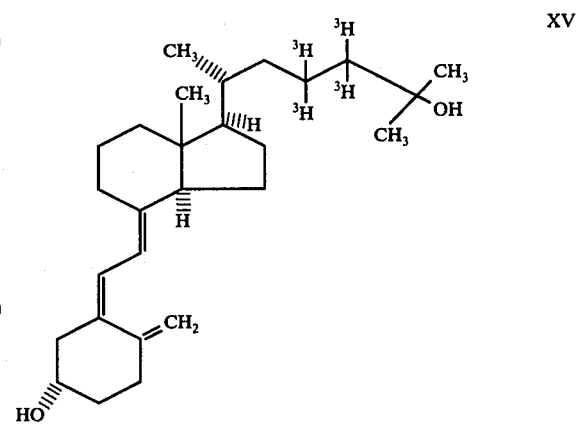

having a specific activity greater than about 30 Ci/mmole, preferably about 92 Ci/mmole.

25-Hydroxycholecalciferol-23,24-$^3$H is useful as a radiolabel for the radio-immunological determination of 25-hydroxycholecalciferol, the initial metabolite of cholecalciferol, vitamin $D_3$, see M. Gemeiner, Mikrochemica Acta [Vienna], 161 (1976).

The following examples are illustrative only of the invention and are not to be construed as limiting the invention in any manner.

EXAMPLE 1

3β,25-Dihydroxycholest-5-en-23-yne diacetate

6β-Methoxy-25-(2-tetrahydropyranyloxy)-3α,5-cyclo-5α-cholest-23-yne (719 mg.) in glacial acetic acid (3 ml.) was heated to 70° C. for 6 hours under nitrogen. After concentration in vacuo, the residue was taken up in 10 ml. acetic anhydride-pyridine (1:1) and kept at 100° C. overnight (18 hours.). Evaporation in vacuo gave a residue which was purified by column chromatography (90 g. silica gel, benzene eluent). Combination of the appropriate fractions (tlc, silica gel, 15% ethyl acetate/hexane) yielded 462 mg. (64%) of product, m.p. 97°-99° C.

Anal. Calcd. for $C_{31}H_{46}O_4$: C, 77.14; H, 9.61. Found: C, 76.92; H, 9.57.

EXAMPLE 2

25-Hydroxylcholesterol diacetate-23,24-$^3$H.

3β,25-Dihydroxycholest-5-en-23-yne-diacetate (11.7 mg., 0.024 mmol) was dissolved in tetrahydrofuran (freshly distilled from sodium, 0.8 ml.) in a system having a total volume of 3.5 cc. 10% palladium on carbon catalyst (fresh, 8.4 mg.) was added. After evacuation, 2.05 cc. of tritium gas (0.093 mmol, 5.70 Ci) was admitted and the system first isolated, then stirred at room temperature for 2 hours. An additional 1.55 cc. (0.070 mmol, 4.30 Ci) of tritium gas was admitted with the stirring continuing overnight. Any unreacted tritium gas was then removed and the sample filtered (rinsing with tetrahydrofuran, 4 × 1 ml.). The filtrate was concentrated to dryness by vacuum transfer and any labile activity removed by successive methanol washes (3 × 1 ml., vacuum transfer). The residue was stored in 100 ml. of toluene (distilled at −20° C.

EXAMPLE 3

25-Hydroxy-7-dehydrocholesterol-23,24-³H.

25-Hydroxycholesterol diacetate-23,24-³H (~2.53 Ci, 11 mg.) was heated to reflux for 20 minutes in hexane (2 ml.) under nitrogen with 18 mg. of 1,3-dibromo-5,5-dimethylhydantoin and 30 mg. of sodium bicarbonate. Filtration of the slurry and concentration in vacuo of the hexane gave a residue which was taken up in xylene (2 ml. containing 200 μl of collidine) and heated to reflux 1½ hours under nitrogen. The solution was concentrated in vacuo, taken up in ethyl acetate and filtered through a short silica gel column. After concentration of the ethyl acetate solution in vacuo, this residue was dissolved in dry ether (1 ml.) and treated with a small amount of lithium aluminum hydride (15 minutes, 0° C.). The excess hydride was decomposed with a few drops of water and the supernatant ether layer decanted and concentrated. The residue was taken up in 250 μl of chloroform, applied to a Sephadex LH-20 column (1¼ × 70 cm, packed and eluted with chloroform/hexane, 65:35) and fractions (2.4 ml.) were collected. Ultraviolet spectra ($\lambda_{max}$282 nm) and tlc analysis (10% AgNO₃/silica gel; 20% acetone/chloroform) indicated the pure 5,7-diene to be in fractions 31–35. Combination of these fractions yielded 153.7 mCi of material. Rechromatography of fractions 28–30, which contained the 5,7-diene contaminated with the 4,6-diene ($\lambda_{max}$239 nm) yielded an additional 76.4 mCi of product.

The combined fractions were assayed by ultraviolet spectra ($\lambda_{max}$282 nm, 1.0 mg.) and liquid scintillation counting (230.1 mCi) to give a specific activity of 92 Ci/mmol (230.1 μCi/ug). The entire sample was stored in 100 ml. toluene (distilled) at −20° C.

EXAMPLE 4

25-Hydroxycholecalciferol-23,24-³H

25-Hydroxy-7-dehydrocholesterol (230.1 mCi, 1.0 mg) was irradiated for 5 minutes at 0° C. in a quartz tube (1 × 30 cm, vigorously flushed with argon) attached to the exterior side of a double wall, water cooled quartz immersion well in which a Hanovia medium pressure quartz, mercury-vapor lamp (450 watts) was placed. The solution was concentrated below room temperature in vacuo and applied in 300 μl of chloroform to a Sephadex LH-20 column (1¼ × 70 cm, packed and developed in chloroform/hexane, 65:35). Fractions (2.4 ml.) were collected and analyzed by ultraviolet absorption ($\lambda_{max}$262 nm) and tlc (10% silver nitrate/silica gel; 20% acetone in chloroform, $R_f$ = 0.56). Fractions 22 through 25 yielded 34 mCi (147.8 μg) of 25-hydroxyprecholecalciferol.

The previtamin (34 mCi, 147.8 μg) in 100 ml. of toluene was heated to 100° C. under nitrogen for 1 hour. The solution was concentrated in vacuo and applied in 300 μl of chloroform to a Sephadex LH-20 column (1¼ × 70 cm, packed and developed in chloroform/hexane, 65:35). Fractions (2.4 ml.) were collected and analyzed by ultraviolet absorption ($\lambda_{max}$265 nm) and tlc (10% silver nitrate/silica gel; 20% acetone in chloroform, $R_f$ = 0.52). Fractions 26–30 yielded 9.01 mCi (39.17 μg) of 25-hydroxycholecalciferol.

We claim:

1. A process for the preparation of a compound of the formula

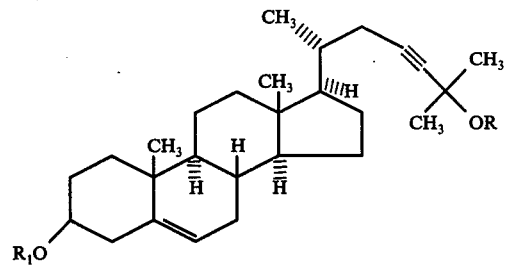

wherein R and $R_1$ are each independently lower alkanoyl which comprises (a) contacting a compound of the formula

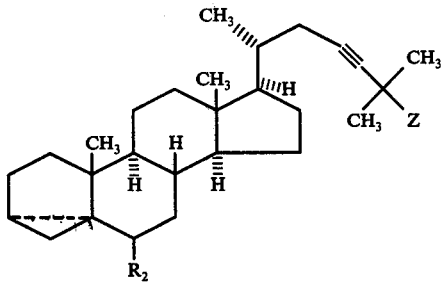

wherein $R_2$ is hydroxy, lower alkoxy, phenyl lower alkoxy, lower alkanoyloxy or benzoyloxy and Z is hydroxy or a group of the formula

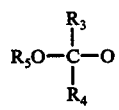

wherein $R_3$ is hydrogen or lower alkyl, $R_4$ and $R_5$ are each independently lower alkyl and $R_4$ and $R_5$ taken together are lower alkylene of from 3 to 8 carbon atoms with a lower alkanoic acid of the formula $R_1$OH wherein $R_1$ is lower alkanoyl to afford a compound of the formula

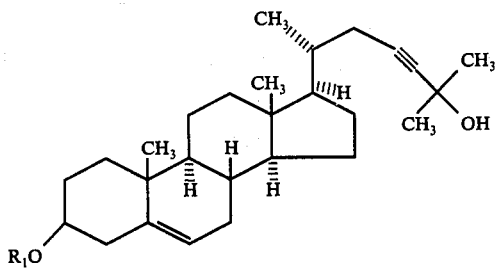

wherein $R_1$ is as above
(b) contacting the compound obtained in step (a) with a lower alkanoic acid anhydride of the formula $(R)_2O$ wherein R is as above in the presence of an acid acceptor and
(c) recovering the product.

2. The process of claim 1 wherein R and $R_1$ are the same lower alkanoyl, $R_2$ is lower alkoxy, $R_3$ is hydrogen and $R_4$ and $R_5$ taken together are lower alkylene.

3. The process of claim 2 wherein R and $R_1$ are acetyl, $R_2$ is alkoxy and $R_4$ and $R_5$ taken together are n-butylene.

4. The process of claim 1 wherein the alkanoic acid is acetic acid.

5. The process of claim 1 wherein the alkanoic acid anhydride is acetic anhydride.

6. The process of claim 1 wherein the acid acceptor is a tertiary amine.

7. The process of claim 6 wherein the tertiary amine is pyridine.

* * * * *